United States Patent
Inoue et al.

(10) Patent No.: US 6,475,506 B1
(45) Date of Patent: Nov. 5, 2002

(54) INFUSION PREPARATION

(75) Inventors: Tadaaki Inoue, Osaka (JP); Hideto Kodaira, Osaka (JP); Yoshihito Nawa, Osaka (JP); Ryoichiro Murashima, Osaka (JP); Shunichi Abe, Osaka (JP); Kazumasa Yokoyama, Osaka (JP)

(73) Assignee: Yoshitomi Pharmaceutical

( * ) Notice: Subject to any disclaimer, the term of this patent is extended or adjusted under 35 U.S.C. 154(b) by 0 days.

(21) Appl. No.: 09/244,931

(22) Filed: Feb. 10, 1999

Related U.S. Application Data

(62) Division of application No. 08/475,812, filed on Jun. 7, 1995, now Pat. No. 5,972,367, which is a division of application No. 08/133,792, filed on Oct. 8, 1993, now abandoned, which is a continuation of application No. 07/873,229, filed on Apr. 24, 1992, now abandoned.

(30) Foreign Application Priority Data

| Apr. 26, 1991 | (JP) | 3-124866 |
| Apr. 27, 1991 | (JP) | 3-124863 |
| Apr. 28, 1991 | (JP) | 3-124739 |
| Jul. 26, 1991 | (JP) | 3-209944 |
| Jul. 26, 1991 | (JP) | 3-209945 |
| Jul. 26, 1991 | (JP) | 3-209946 |
| Jul. 26, 1991 | (JP) | 3-209947 |
| Aug. 6, 1991 | (JP) | 3-222031 |
| Aug. 6, 1991 | (JP) | 3-222032 |
| Jan. 17, 1992 | (JP) | 4-27338 |

(51) Int. Cl.$^7$ .............................................. A61K 9/107
(52) U.S. Cl. ........................ 424/422; 424/423; 514/938; 426/602
(58) Field of Search ................................. 424/423, 422, 424/502; 514/951, 938; 426/602

(56) References Cited

U.S. PATENT DOCUMENTS

| 4,290,910 A | 9/1981 | Harada et al. ............... 252/312 |
| 4,387,109 A | * 6/1983 | Kahn et al. |
| 4,970,209 A | 11/1990 | Wretlind et al. ............. 514/221 |
| 5,229,422 A | 7/1993 | Takahashi et al. ........... 514/558 |

* cited by examiner

Primary Examiner—Edward J. Webman
(74) Attorney, Agent, or Firm—Sughrue Mion, PLLC

(57) ABSTRACT

Disclosed is an infusion preparation for nutrient supply use. It comprises a sugar, amino acids, electrolytes and a fat emulsion. It has an excellent shelf life without causing precipitation, denaturation and the like in spite of the simultaneous presence of these components. Also disclosed is a container filled with infusion liquids comprising a first and a second compartment separated from each other by a separation means, wherein an infusion liquid containing a fat emulsion and a sugar is included in the first compartment and another infusion liquid containing amino acids and electrolytes is included in the second compartment. Further disclosed are an infusion preparation comprising a fat emulsion and a sugar, and an infusion preparation comprising amino acids and electrolytes. An infusion preparation containing a sugar, amino acids, electrolytes and a fat emulsion can be obtained easily and aseptically upon use, by simply removing a separation means attached to the container and mixing the two infusion liquids.

13 Claims, 2 Drawing Sheets

INFUSION PREPARATION

This application is a Divisional application of U.S. Ser. No. 08/475,812, filed Jun. 7, 1995, now U.S. Pat. No. 5,972,367, in turn a Divisional application of U.S. Ser. No. 08/133,792, filed Oct. 8, 1993, now abandoned in turn a Continuation application of U.S. Ser. No. 07/873,229 filed Apr. 24, 1992 now abandoned. U.S. Pat. No. 5,626,880 is based on U.S. Ser. No. 08/589,207 filed Jan. 22, 1996 as a Continuation application of U.S. Ser. No. 08/133,792. U.S. Pat. No. 5,674,527 is based on U.S. Ser. No. 08/478,970, filed Jun. 7, 1995 as a Divisional application of U.S. Ser. No. 08/133,792.

FIELD OF THE INVENTION

This invention relates to infusion preparations, more particularly to an infusion preparation which comprises a sugar, amino acids, electrolytes and a fat emulsion. The preparation has excellent stability and shelf life. This invention also relates to a container for use in making these infusion preparations, an infusion preparation containing a fat emulsion and a sugar, and an infusion preparation containing amino acids and electrolytes.

BACKGROUND OF THE INVENTION

Intravenous infusion is carried out for the purpose of supplying nutrients to maintain a patient's life when oral or nasal feeding is impossible or insufficient, when the digestion and absorption functions of the patient are in a poor state even if such a feeding means can be carried out, or when the passage of food through the digestive tract makes the patient's condition or disease more serious.

Examples of commercially available infusion preparations include a sugar infusion liquid which contains reducing sugars and the like, an amino acid infusion liquid which contains essential amino acids and the like, an electrolyte infusion liquid which contains electrolytes and the like, a fat emulsion which contains a plant oil emulsion and the like, and a vitamin mixture. These infusion preparations are appropriately selected depending on the condition of the patient and are mixed upon use.

However, mixing these preparations at the time of their use requires complex handling and, above all things, raises the problem of microbial contamination. With the aim of overcoming such problems, various infusion preparations in which some of the aforementioned ingredients are mixed in advance have been proposed. Infusion preparations which contain sugars, amino acids, electrolytes and fat emulsions, all being essential nutrients to be supplied, are especially useful from a clinical point of view.

However, since these sugar liquids, amino acid liquids, electrolyte liquids and fat emulsion are different from one another in terms of the conditions for their stable existence, various problems arise when they are mixed and the mixture becomes useless in many cases.

For example, because of its unstable nature, a fat emulsion is apt to form bulky fat particles and to cause phase separation (creaming) when mixed with other infusion liquids. In particular, divalent cations in an electrolyte infusion liquid cause aggregation and disintegration of fat emulsion particles.

In the case of an electrolyte infusion liquid, since it contains calcium and phosphoric acid as essential components to maintain the balance of electrolytes, it is apt to form calcium phosphate by the reaction of calcium with phosphoric acid and therefore to generate turbidity and precipitation. In order to prevent the formation of turbidity and precipitation, such an electrolyte infusion liquid is usually adjusted to a low pH value (less than pH 5). When such a electrolyte infusion liquid is mixed with an amino acid infusion liquid, the pH of the mixture increases to the amino acid pH value because of the strong buffer action of amino acids, thus requiring a large quantity of acidic materials (for example, hydrochloric acid, acetic acid and the like) to keep the pH value at a low level. However, acid materials can be used only in a limited amount because a large quantity of acid spoils the balance of the infusion components. As a consequence, the pH value of the mixture of electrolyte and amino acid infusion liquids cannot be lowered to a satisfactory level, thus resulting in the generation of turbidity and precipitation at the time of heat sterilization of the mixture.

In addition, when a mixture of an amino acid infusion liquid with a sugar infusion liquid is sterilized by heating, considerable coloring occurs due to the Maillard's reaction.

As described above, it is difficult to prepare a storable infusion preparation which contains a sugar, amino acids, electrolytes and a fat emulsion in advance, because mixing these different types of infusion liquids or emulsions causes various problems such as precipitation, phase separation, denaturation, coloring and the like. Because of these problems, a fat emulsion, a sugar infusion liquid, an amino acid infusion liquid and an electrolyte infusion liquid are ordinarily mixed upon use. As a consequence, an infusion preparation which contains a sugar, amino acids, electrolytes and a fat emulsion and can be stably stored has been desired.

SUMMARY OF THE INVENTION

Under these circumstances, the present inventors have conducted intensive studies on the development of a stable infusion preparation which contains a sugar, amino acids, electrolytes and a fat emulsion. They have found that, even in the case of an infusion preparation containing all these components, problems such as precipitation, phase separation, denaturation, coloring and the like can be solved by improving the properties of each component and by certain other modifications.

Further, as a result of intensive investigation on a process for preparing such an infusion preparation, it has been found that preparations containing the above components in a certain combination can be stably stored and a desired infusion preparation can be easily obtained upon use by mixing the above preparations without suffering precipitation, denaturation, coloring and other problems.

An object of the present invention is to provide an infusion preparation which contains a sugar, amino acids, electrolytes and a fat emulsion, has excellent stability and can be stored stably.

Another object of the present invention is to provide a container filled with infusion liquids, which is useful for mixing an infusion preparation.

Another object of the present invention is to provide an infusion preparation containing a fat emulsion and a sugar.

Another object of the present invention is to provide an infusion preparation containing amino acids and electrolytes.

BRIEF DESCRIPTION OF THE DRAWINGS

In FIGS. 1 and 2, the reference numerals 1 and 11 identify the suspective containers, 2 and 12 identify first compartments, 3 and 13 identify second compartments, 4 and 14 identify infusion liquid containing fat emulsions and sugars, 5 and 15 identify infusion liquid containing amino acids and electrolytes, 6 identifies a communicating means, 7 and 16 identify a separation means and 8, 9, 10, 17, 18 and 19 identify ports.

In FIG. 3, a symbol ● stands for glycerol, ◆ stands for glucose, ♦ stands for sorbitol, □ stands for xylitol, ▽ stands for fructose and ▼ stands for a control.

DETAILED DESCRIPTION OF THE INVENTION

Figure 1:
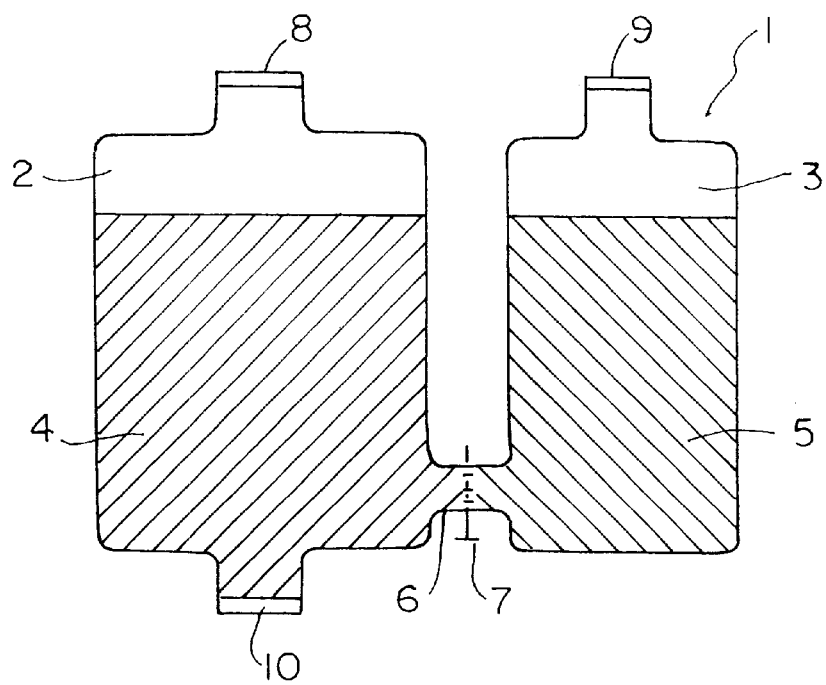
FIG. 1 is a cross-section of an example of a container of the present invention filled with infusion liquids.

The present invention relates to an infusion preparation comprising a sugar, amino acids, electrolytes and a fat emulsion, said preparation contains phosphorus in the form of a phosphoric ester of a polyhydric alcohol or a sugar or as a salt of the ester, and is adjusted to a pH value of from 5.0 to 8.0 with an organic acid. The present invention also relates to a container filled with infusion liquids, which is useful for mixing the infusion preparation. Further, the present invention relates to an infusion preparation containing a fat emulsion and a sugar, and an infusion preparation containing amino acids and electrolytes.

In particular, it is preferable to use a fat emulsion which has a mean particle size of 0.17 μm or less. The phosphorus source of the electrolyte is preferably a phosphoric ester of a polyhydric alcohol or a sugar or a salt of the ester.

The container of the present invention filled with infusion liquids is a container which comprises first and second compartments separated from each other by a separation means. The infusion liquid containing a fat emulsion and a sugar is included in the first compartment, and another infusion liquid containing amino acids and electrolytes is included in the second compartment.

Various types of sugars may be used in the present invention. Reducing sugars such as glucose, fructose, maltose and the like are particularly preferred. These reducing sugars may be used alone or as a mixture of two or more. These reducing sugars may be mixed further with at least one compound selected from the group consisting of sorbitol, xylitol, glycerol and the like.

Examples of the amino acids used in the present invention include various essential and non-essential amino acids which have been used in the conventional amino acid infusion preparations for supplying the living body with nutrients, such as L-isoleucine, L-leucine, L-valine, L-lysine, L-methionine, L-phenylalanine, L-threonine, L-tryptophan, L-arginine, L-histidine, glycine, L-alanine, L-proline, L-aspartic acid, L-serine, L-tyrosine, L-glutamic acid, L-cysteine and the like. These amino acids may be used not only as free amino acid forms but also in various other forms which include for instance: inorganic acid salts such as L-lysine hydrochloride and the like; organic acid salts such as L-lysine acetate, L-lysine malate and the like; esters which can be hydrolyzed in vivo such as L-tyrosine methyl ester, L-methionine methyl ester, L-methionine ethyl ester and the like; N-substituted derivatives such as N-acetyl-L-tryptophan, N-acetyl-L-cysteine, N-acetyl-L-proline and the like; and dipeptides of the same or different amino acids such as L-tyrosyl-L-tyrosine, L-alanyl-L-tyrosine, L-arginyl-L-tyrosine, L-tyrosyl-L-arginine and the like.

Various types of water soluble salts which have been used in the prior art infusion preparations can be used as electrolytes of the present invention, including chlorides, sulfates, acetates, gluconates, lactates and the like, water soluble salts of various inorganic components such as sodium, potassium, calcium, magnesium, zinc, iron, copper, manganese, iodine, phosphorus and the like, which are considered to be essential for the maintenance of biological functions and electrolyte balance in the body fluid. Hydrates of these water soluble salts may also be used.

In these electrolyte components, phosphoric esters of polyhydric alcohols or sugars or salts thereof may be used suitably as the source of phosphorus. Examples of phosphoric esters of polyhydric alcohols include glycerophosphoric acid, mannitol-1-phosphoric acid, sorbitol-1-phosphoric acid and the like. Examples of phosphoric esters of sugars include glucose-6-phosphoric acid, mannose-6-phosphoric acid and the like. As salts of these phosphoric esters, alkali metal salts such as sodium salt, potassium salt and the like and alkaline earth metal salts such as magnesium salt may be used. Preferred examples of phosphoric ester salts include a sodium salt and a potassium salt of glycerophosphoric acid.

The preferred electrolyte components are as follows:

Sodium: sodium chloride, sodium lactate, sodium acetate, sodium sulfate and sodium glycerophosphate;

Potassium: potassium chloride, potassium glycerophosphate, potassium sulfate, potassium acetate and potassium lactate;

Calcium: calcium gluconate, calcium chloride, calcium glycerophosphate, calcium lactate, calcium pantothenate and calcium acetate;

Magnesium: magnesium sulfate, magnesium chloride, magnesium glycerophosphate, magnesium acetate and magnesium lactate;

Phosphorus: potassium glycerophosphate, sodium glycerophosphate, magnesium glycerophosphate and calcium glycerophosphate; and Zinc: zinc sulfate, zinc chloride, zinc gluconate, zinc lactate and zinc acetate.

The fat emulsion of the present invention may be an oil-in water type emulsion which is prepared by dispersing a fat in water using an emulsifying agent. The fat emulsion may be prepared in any suitable way, for example by adding a fat and an emulsifying agent to water, stirring the mixture to prepare a crude emulsion and then emulsifying the crude emulsion by any commonly used means such as a high pressure emulsification method.

When the emulsion is prepared by a high pressure emulsification method, the crude emulsion may be passed 5 to 50 times through a homogenizer such as a Manton-Gaulin homogenizer at a pressure condition of generally from 20 to 700 kg/cm$^2$.

Any edible fats and oils can be used as the fat source of the fat emulsion. Preferred examples of the fat sources include: plant oils such as soybean oil, cotton oil, safflower oil, corn oil, coconut oil, perilla oil and the like; fish oils such as cod liver oil and the like; medium-chain fatty acid triglycerides such as Panacet (trade name), ODO (trade name) and the like; and chemically defined triglycerides such as 2-linoleoyl-1,3-dioctanoyl glycerol (8L8), 2-linoleoyl-1,3-didecanoyl glycerol (10L10) and the like. These fats and oils may be used alone or as a mixture of two or more.

Any emulsifying agent commonly used in pharmaceutical preparations may be used in the present invention. One or more agents may be used which are preferably selected from the group consisting of egg yolk phospholipids, hydrogenated egg yolk phospholipids, soybean phospholipids, hydrogenated soybean phospholipids and nonionic surface active agents such as Pluronic F68 (trade name, polyoxyethylenepolyoxypropylene block co-polymer) and HCO-60 (trade name, polyoxyethylene hydrogenated castor oil).

A fat emulsion prepared from soybean oil as the fat source and egg yolk phospholipid as the emulsifying agent are particularly preferred.

According to the present invention, the fat emulsion may preferably be prepared so that its mean particle size becomes 0.17 µm or less. By controlling the particle size at this level, higher stability of the fat emulsion than those of currently used fat emulsions (mean particle sizes, 0.2 to 0.3 µm) can be achieved and phase separation in the fat emulsion caused by a difference in specific gravities can be prevented effectively.

A fat emulsion having a mean particle size of 0.17 µm or less can be prepared by adding at least one compound selected from glycerol and glucose followed by emulsification. According to this technique, a fat emulsion having a mean particle size of 0.17 µm or less can be prepared easily because of the specific capacity of glycerol and glucose to enhance formation of fine particles.

More illustratively, such a fat emulsion can be prepared for example by adding to water a fat source and an emulsifying agent together with glycerol and/or glucose, stirring the mixture to obtain a crude emulsion and then emulsifying the crude emulsion by a conventional method such as the aforementioned high pressure emulsification method. In this instance, glycerol and/or glucose may be added at the time of the emulsification. For example, glycerol and/or glucose may be added to a crude emulsion prepared from a fat and an emulsifying agent.

Mean particle size of the thus prepared emulsion can be determined by a conventional method such as a light scattering method.

In the above-described emulsion preparation process, a fat, an emulsifying agent and glycerol and/or glucose may be used in such amounts that the resulting fat emulsion consists of the fat in an amount of from 0.1 to 30% by w/v (unless otherwise noted, the term "%" as used hereinafter means w/v %), preferably from 1 to 20%, the emulsifying agent in an amount of from 0.01 to 10%, preferably from 0.05 to 5%, the glycerol and/or glucose in an amount of from 30 to 70%, preferably from 40 to 60% and water in an appropriate amount.

Types, mixing ratios and concentrations of sugars, amino acids, electrolytes and fat emulsions to be used in the infusion preparation of the present invention can be adjusted depending on the use of the preparation, the diseases and symptoms of the patient and other conditions. The following illustrates preferred composition of the infusion preparation of the present invention:

The Fat Emulsion and the Sugar

| fat | 5–50 g/l |
|---|---|
| emulsifying agent | 0.5–10 g/l |
| sugar | 50–250 g/l |

The Amino Acids and the Electrolytes

| L-isoleucine | 0.5–5 g/l |
|---|---|
| L-leucine | 0.5–7 g/l |
| L-valine | 0.5–5 g/l |
| L-lysine | 0.5–7 g/l |
| L-methionine | 0.1–4 g/l |
| L-phenylalanine | 0.3–5 g/l |
| L-threonine | 0.3–5 g/l |
| L-tryptophan | 0.1–1 g/l |
| L-arginine | 0.3–7 g/l |
| L-histidine | 0.2–3 g/l |
| glycine | 0.2–3 g/l |
| L-alanine | 0.3–5 g/l |
| L-proline | 0.2–5 g/l |
| L-aspartic acid | 0.03–2 g/l |
| L-serine | 0.2–3 g/l |
| L-tyrosine | 0.03–0.5 g/l |
| L-glutamic acid | 0.03–2 g/l |
| L-cysteine | 0.03–1 g/l |
| sodium | 15–60 mEq/l |
| potassium | 10–50 mEq/l |
| calcium | 3–15 mEq/l |
| magnesium | 2–10 mEq/l |
| chlorine | 0–80 mEq/l |
| phosphorus | 1–15 mmol/l |
| zinc | 0–30 µmol/l |

The infusion preparation of the present invention may be prepared by dissolving or dispersing each of the above components in purified water (for example, distilled water for injection and the like) or, preferably, by individually preparing a sugar liquid, an amino acid liquid, an electrolyte liquid and a fat emulsion, sterilizing each of the thus-prepared liquids and emulsion by heat sterilization or the like and then aseptically mixing appropriate volumes of the sterilized infusion liquids and emulsion with such a mixing ratio that the concentration of each component is adjusted to a predetermined level.

The sugar liquid, amino acid liquid and electrolyte liquid can be prepared in a conventional manner and the fat emulsion can be prepared by the aforementioned method. Each of the thus prepared infusion liquids and emulsion is put into a glass or plastic container. The atmosphere in the container is replaced with an inert gas such as nitrogen, helium or the like and then the resulting container is sealed and subjected to an appropriate sterilization treatment. In this instance, the glass or plastic container may be in the form of a bag, a bottle or the like made of polypropylene, polyethylene, ethylene-vinyl acetate copolymer, polyvinyl chloride or the like. The sterilization may be effected in a common way, for example, by a heat sterilization treatment such as high-pressure steam sterilization, hot water immersion sterilization, hot water shower sterilization or the like. When plastic containers are used, it is preferable to carry out their sterilization in an atmosphere which is substantially free from oxygen.

The container filled with infusion liquids according to the present invention comprises a sealed container which comprises two compartments capable of communicating with each other through a communicating means. These two compartments are separated from each by a separation means attached to the communicating means. An infusion liquid containing a fat emulsion and a sugar is enclosed in the first compartment, and another infusion liquid containing amino acids and electrolytes is enclosed in the second compartment, followed by immediate heat sterilization. At the time of use, an infusion preparation is obtained by withdrawing the separation means to allow the first and second compartments to communicate each other, thereby mixing the two liquids through the communicating means.

FIG. 1 is a cross-sectional illustration showing an example of a container of the present invention filled with infusion liquids. In this figure, a container 1 made of a plastic material has two compartments, that is, a first compartment 2 and a second compartment 3. An infusion liquid 4 containing a fat emulsion and a sugar is enclosed in the first compartment 2, and another infusion liquid 5 containing amino acids and electrolytes is enclosed in the second compartment 3. The first and second compartments 2 and 3 are separated from each other by a separation means 7 (a pinch cock in this case) attached to a communicating means 6, in order to prevent mixing of the infusion liquid 4 enclosed in the first compartment 2 with the infusion liquid 5 enclosed in the second compartment 3. In addition, the container 1 is equipped with a port 8 for use in the injection of the infusion liquid 4 into the first compartment 2, a port 9 for use in the injection of the infusion liquid 5 into the second compartment 3 and a port 10 for use in the ejection of a mixed preparation. If necessary, admixing other agents may be effected through these ports.

This container filled with infusion liquids is obtained in the following manner. First, the communicating means 6 of the container 1 is shut off by a separation means (pinch cock 7 in this case) to separate the first and second compartments 2 and 3 from each other, followed by the injection of an infusion liquid containing a fat emulsion and a sugar into the first compartment 2 through the port 8 and the injection of another infusion liquid containing amino acids and electrolytes into the second compartment 3 through the port 9. In this instance, it is preferable to carry out the injection of the infusion liquids 4 and 5 into the first and second compartments 2 and 3 under a stream of an inert gas such as nitrogen, argon or the like. When the injection of the infusion liquids 4 and 5 into the first and second compartments 2 and 3 is completed, the ports 8 and 9 are sealed and the resulting container is sterilized to obtain the infusion liquids-enclosed container of FIG. 1. The sterilization may be effected in any common way, for example, by a heat sterilization means such as high-pressure steam sterilization, hot water immersion sterilization, hot water shower sterilization or the like. When a plastic containers is used as in this case, it is preferable to carry out its sterilization in an atmosphere which is substantially free from oxygen.

The thus-obtained infusion liquids-enclosed container of the present invention can be stored as it is. An infusion preparation containing a fat emulsion, a sugar, amino acids and electrolytes can be aseptically mixed at the time of use by removing the pinch cock 7 to allow the first and second compartments 2 and 3 to communicate each other and mixing the infusion liquids 4 and 5 enclosed in the compartments. Thereafter, the thus mixed infusion preparation is ejected aseptically from the port 10 and administered to the living body through a tube (not shown in the figure).

Figure 2:
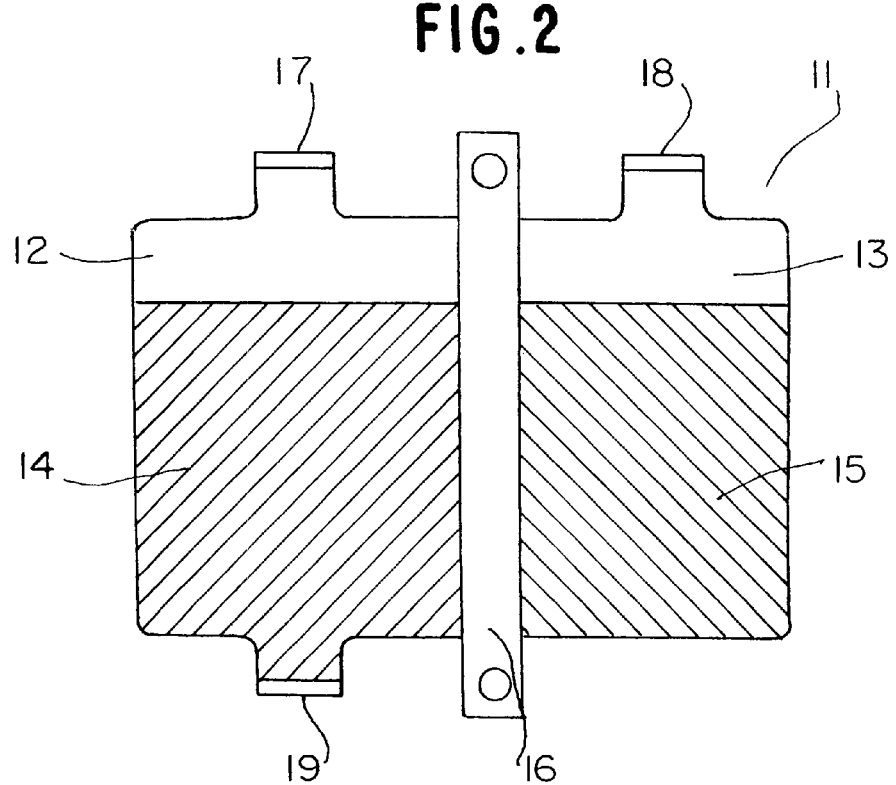
FIG. 2 is a cross-section of another example of a container of the present invention filled with infusion liquids.

FIG. 2 is a cross-sectional illustration showing another example of a container of the present invention filled with infusion liquids. In this figure, a rectangular container 11 made of a plastic material and other materials has two compartments, that is, a first compartment 12 and a second compartment 13 which are separated from each other by a large screw cock 16. An infusion liquid 14 containing a fat emulsion and a sugar is enclosed in the first compartment 12 and another infusion liquid 15 containing amino acids and electrolytes is enclosed in the second compartment 13. Since the first and second compartments 12 and 13 are separated from each other by the screw cock 16, the infusion liquid 14 enclosed in the first compartment 12 and the infusion liquid 15 enclosed in the second compartment 13 are not mixed. In addition, the container 11 is equipped with a port 17 for use in the injection of the infusion liquid 14 into the first compartment 12, a port 18 for use in the injection of the infusion liquid 15 into the second compartment 13 and a port 19 for use in the ejection of mixed preparation. If necessary, admixing of other agents may be effected through these ports. The production process and use of the container filled with infusion liquids shown in FIG. 2 are substantially the same as those of the container shown in FIG. 1. Mixture of the infusion liquids 14, 15 is accomplished by turning the screw cock 16.

The infusion liquids-enclosed containers shown in FIGS. 1 and 2 are only an aspect of the present invention and are not to be construed as limiting the invention. Shape, size and the like of the container can be changed at will, as well as the separation means. For example, in FIG. 1, a clip may be used instead of the pinch cock 7, or the first and second compartments 2 and 3 may be separated from each other by installing a ball cock inside the communicating means 6. A heat fusible film or a breakable connector may also be used.

In the above process, the infusion liquid containing a fat emulsion and a sugar to be enclosed in the first compartment may be prepared by various means. For example, a sugar may be added to a fat emulsion which has been prepared by the aforementioned procedure, or in advance to a fat/emulsifier mixture to be emulsified. Preferably, a sugar is added to a fat at the time of preparation of the fat emulsion so that a mean particle size of the fat emulsion may be 0.17 $\mu$m or less. Such a fat emulsion can be prepared as described above. The composition of the infusion liquid containing a fat emulsion and a sugar can be varied optionally depending on the concentration of the infusion liquid to be enclosed in the second compartment (that is, the infusion liquid containing amino acids and electrolytes), the volumetric ratio of the liquids to be injected into the first and second compartments, and the like. A preferred example of the composition may consist of a fat in an amount of from 0.1 to 30%, preferably from 1 to 20%, more preferably from 2 to 10%, an emulsifying agent in an amount of from 0.01 to 10%, preferably from 0.05 to 5%, more preferably from 0.1 to 1%, a reducing sugar in an amount of from 5 to 60%, preferably from 7 to 40%, more preferably from 10 to 30% and water in an appropriate amount.

The infusion liquid containing amino acids and electrolytes to be enclosed in the second compartment may be prepared by various means. For example, each of the amino acids and electrolytes to be blended may be dissolved in purified water such as distilled water for injection. Composition of the infusion liquid containing amino acids and electrolytes can be varied optionally depending on the concentration of the infusion liquid to be enclosed in the first compartment (that is, an infusion liquid containing a fat emulsion and a sugar), the volumetric ratio of liquids to be injected into the first and second compartments and the like. A preferred example of the composition may consist of amino acids in a total amount of from 1 to 15%, preferably from 2 to 13%, more preferably from 3 to 12% and, as electrolytes, 50 to 180 mEq/l of sodium, 40 to 135 mEq/l of potassium, 10 to 50 mEq/l of calcium, 5 to 30 mEq/l of magnesium, 0 to 225 mEq/l of chlorine, 3 to 40 mmol/l of phosphorus and 0 to 100 $\mu$mol/l of zinc, in addition to a suitable quantity of water.

A preferred composition is as follows:

The Electrolytes

| | |
|---|---|
| sodium | 50–180 mEq/l |
| potassium | 40–135 mEq/l |
| calcium | 10–50 mEq/l |
| magnesium | 5–30 mEq/l |
| chlorine | 0–225 mEq/l |
| phosphorus | 3–40 mmol/l |
| zinc | 0–100 µmol/l |

The Amino Acid

| | |
|---|---|
| L-isoleucine | 1–15 g/l |
| L-leucine | 1–20 g/l |
| L-valine | 1–15 g/l |
| L-lysine hydrochloride | 1–20 g/l |
| L-methionine | 0.5–10 g/l |
| L-phenylalanine | 1–15 g/l |
| L-threonine | 1–15 g/l |
| L-tryptophan | 0.3–3 g/l |
| L-arginine | 1–20 g/l |
| L-histidine | 0.5–10 g/l |
| glycine | 0.5–10 g/l |
| L-alanine | 1–15 g/l |
| L-proline | 0.5–15 g/l |
| L-aspartic acid | 0.1–5 g/l |
| L-serine | 0.5–10 g/l |
| L-tyrosine | 0.1–1 g/l |
| L-glutamic acid | 0.1–5 g/l |
| L-cysteine | 0.1–3 g/l |

The pH value of the infusion preparation of the present invention may be adjusted to from 5.0 to 8.0, preferably from 5.5 to 7.5, from the view point of safety to the living body. Especially, when a phosphoric ester of a polyhydric alcohol or a sugar or a salt of the ester is used as the source of phosphorus, precipitation can be prevented effectively even at a relatively high pH value.

Various acid materials, preferably organic acids, may be used as agents for adjusting the pH of the infusion preparation as long as they are physiologically acceptable. Examples of the pH-adjusting agents include at least one organic acid selected from the group consisting of citric acid, gluconic acid, lactic acid, malic acid, maleic acid and malonic acid. Of these organic acids, oxycarboxylic acids may be used also in the form of lactone or lactide. Also, these organic acids may be used in their salt forms or as mixtures with their salts. Salts of these organic acids include inorganic base salts (for example, alkali metal salts such as sodium salt, potassium salt and the like) and organic base salts (for example, ethanol amine salt, N-methylglucamine salt, amino acid salt and the like). These organic acids can make the fat emulsion stable to divalent metal ions. Thus, when a fat emulsion is mixed with a solution containing divalent metal ions in the presence of these organic acids, the obtained fat emulsion is so stable that aggregation of fat particles can be prevented. Organic acids which are capable of undergoing chelation of divalent metal ions are desirable, with citric acid being particularly preferred.

Addition of the pH-adjusting agent may be effected at any time. Preferably, however, a predetermined amount of the agent is added in advance to one or both of the infusion liquids such as a sugar infusion liquid. For example, in the case of the container of FIG. 1, the pH-adjusting agent may be added to one or both of the infusion liquids in the first and second compartments.

In order to prevent coloring at the time of sterilization and during storage, an anti-coloring agent such as thioglycerol, dithiothreitol or the like may be added to the infusion preparation of the present invention, generally in an amount of about 1% or less. Addition of the anti-coloring agent may be effected at any time. Preferably, however, a predetermined amount of the agent may be added in advance to one or both of the infusion liquids, such as a sugar infusion liquid. For example, in the case of the container of FIG. 1, the anti-coloring agent may be added in advance to one or both of the infusion liquids in the first and second compartments.

In addition, the infusion preparation of the present invention may be further mixed with vitamins such as vitamin A, the B vitamins, vitamin C, the D vitamins, vitamin E, the K vitamins and the like. Also, the infusion liquid to be enclosed in the first compartment may be mixed with a buffer such as L-histidine, tris(hydroxymethyl)aminomethane or the like in an amount of from 0.001 to 1.0%, preferably from 0.002 to 0.5%, more preferably from 0.005 to 0.3%. L-Histidine and tris(hydroxymethyl)aminomethane may be used alone or in combination, if necessary in the form of salts. Acid addition salts such as hydrochloride and the like are useful as the salts. In the case of L-histidine, metal salts such as sodium salt, potassium salt and the like are also useful. These buffers prevent a decrease in pH and generation of free fatty acids during sterilization and preservation of the infusion preparation. The thus-obtained infusion preparation is stable and has a reduced concentration of free fatty acids.

In order to prevent denaturation of the enclosed components, the container filled with infusion liquids according to the present invention may be wrapped with an oxygen-impermeable film material. Examples of such oxygen-impermeable film materials include: three layer laminate films in which an ethylene-vinyl alcohol copolymer film, a polyvinyl alcohol film, a polyvinylidene chloride film or the like is used as an internal layer (for example, a laminate film which comprises outer layers of a polyester film, a stretched nylon film, a stretched polypropylene film and the like and an internal layer of an un-stretched polypropylene film); laminate films having an aluminum layer (for example, a laminate film having an aluminum layer interposed between a polyester film and an un-stretched polypropylene film); and laminate films having an inorganic material-deposited film (for example, a laminate film having a silicon-deposited film interposed between a polyester film and an un-stretched polypropylene film, a laminate film having a silicon-deposited film interposed between a stretched nylon film and an un-stretched polypropylene film, a laminate film having an aluminium-deposited film interposed between a polyester film and an un-stretched polypropylene film and a laminate film having a polyvinylidene chloride film interposed between an alumina-deposited polyester film and an unstretched polypropylene film).

An oxygen scavenger such as Ageless (trade name) may be put between the wrapping material and the container, or the container wrapped with the film material may be subjected to vacuum packaging or inert gas(nitrogen for example)-charged packaging in the usual way.

The thus-obtained infusion preparation containing a fat emulsion, a sugar, amino acids and electrolytes has an excellent shelf life, is free from precipitation, denaturation, coloring and the like, and can be stored for about one week. The infusion preparation may be administered to a patient by intravenous injection as it is or after being diluted with purified water, if necessary by mixing it with other drugs and the like. It may also be used through other routes of administration such as oral or rectal administration and the like.

The infusion preparation of the present invention which comprises a sugar, amino acids, electrolytes and a fat emulsion does not result in precipitation, phase separation, denaturation, coloring or the like, in spite of the presence of these components in a lump. Thus, the present invention can provide an infusion preparation having excellent stability and safety. In addition, according to the container of the present invention filled with infusion liquids, an infusion liquid containing a fat emulsion and a sugar and another infusion liquid containing amino acids and electrolytes are separately enclosed in advance in two compartments which are separated from each other, and the infusion preparation of the present invention can be obtained by simply removing a separation means attached to the container and mixing the two aseptically enclosed liquids upon use. In other words, by the use of the inventive container, an infusion preparation can be obtained easily and simply without causing microbial contamination at the time of mixing, because it does not require a handling step to mix separately prepared fat emulsion, sugar solution, amino acid solution and electrolyte solution.

The following Examples are given to illustrate further the present invention, but are not to be construed as limiting the scope of the present invention.

EXAMPLE 1

A mixture consisting of 60 g of soybean oil, 7.2 g of egg yolk phospholipid and an appropriate amount of distilled water for injection was stirred using a mixer. The total volume was adjusted to 1,000 ml with distilled water for injection to obtain a crude emulsion. The resulting emulsion was subsequently emulsified using a Manton-Gaulin homogenizer (15M-8TA, manufactured by Gaulin). A 500 ml portion of the thus obtained emulsion was mixed with 250 g of glucose and the total volume was adjusted to 1,000 ml with distilled water for injection. Thereafter, the pH of the resulting emulsion was adjusted to 6 to obtain an infusion preparation. The composition of the thus-obtained infusion preparation is shown in Table 1.

A 50 ml capacity glass container was charged with the infusion preparation, and the air in the container was replaced by nitrogen gas. Thereafter, the container filled with the infusion preparation was sealed and subjected to sterilization by autoclaving at 115° C. for 30 minutes. The appearance, pH values and mean particle sizes of the infusion preparation before and after sterilization are shown in Table 2.

TABLE 1

| Component | Amount (g) |
| --- | --- |
| Soybean oil | 30 |
| Egg yolk phospholipid | 3.6 |
| Glucose | 250 |
| Distilled water for injection | necessary amount to adjust total volume to 1,000 ml |

TABLE 2

| Test item | Before sterilization | After sterilization |
| --- | --- | --- |
| Appearance | white homogeneous emulsion | white homogeneous emulsion |
| pH | 5.60 | 5.03 |
| Mean particle size | 0.22 µm | 0.22 µm |

As shown in Table 2, the infusion preparation maintained a stable emulsion, though its pH value decreased slightly after sterilization.

EXAMPLE 2

An infusion preparation shown in the following Table 3 was obtained in a manner similar to the procedure of Example 1 except for using fructose in place of glucose and sterilized by autoclaving in the same manner as in Example 1. The infusion preparation maintained emulsion in a good state after sterilization.

TABLE 3

| Component | Amount (g) |
| --- | --- |
| Soybean oil | 30 |
| Egg yolk phospholipid | 3.6 |
| Fructose | 250 |
| Distilled water for injection | necessary amount to adjust total volume to 1,000 ml |

EXAMPLE 3

A dispersed system containing soybean oil and egg yolk phospholipid was mixed with glycerol or a sugar (glucose, sorbitol, xylitol or fructose) to obtain a crude emulsion. It was further emulsified with a Manton-Gaulin homogenizer (15M-8TA, manufactured by Gaulin) under a pressure of 550 kg/cm$^2$ and at a temperature of 70° C. or below to obtain a fat emulsion having the composition shown in Table 4.

During the emulsification step, periodical changes in the mean particle size of the emulsion were checked. For the measurement of the mean particle size, 100 ml of water was added to 0.1 ml of each emulsion sample to serve as a sample solution and the mean particle size of the sample solution was measured using a Malvern Autosizer 2C (manufactured by Malvern). As a control, the same procedure was repeated except that glycerol or each sugar was replaced by the same amount of water.

Figure 3:
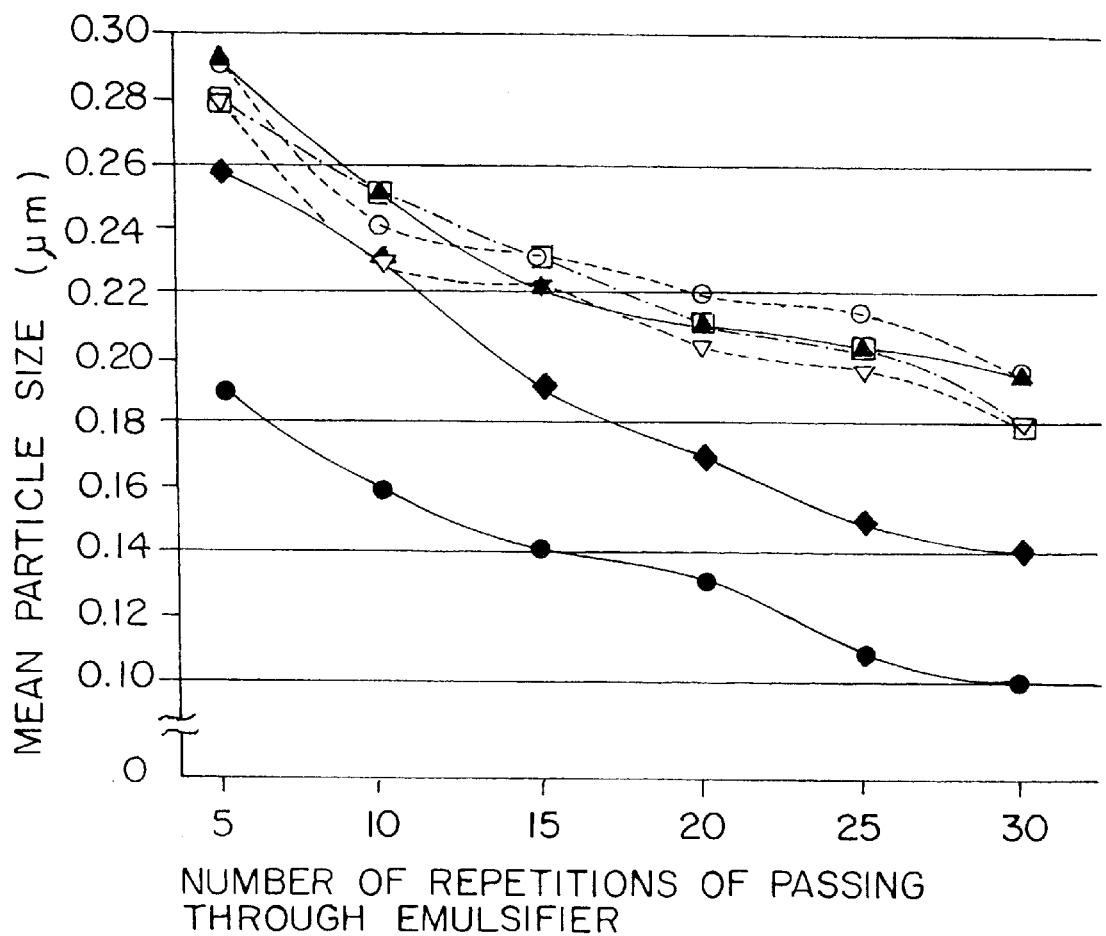
FIG. 3 is a graph showing the relation of the mean particle size of a fat emulsion sample plotted against the number of times a sample passed through an emulsifier with respect to a fat emulsion obtained in Example 3.

The results are shown in FIG. 3 in which a symbol ● stands for glycerol, ◆ stands for glucose, ♦ stands for sorbitol, □ stands for xylitol, ∇ stands for fructose and ▲ stands for a control.

TABLE 4

| Component | Amount (g) |
| --- | --- |
| Soybean oil | 30 |
| Egg yolk phospholipid | 3.6 |
| Glycerol or sugar | 500 |
| Distilled water for injection | necessary amount to adjust total volume to 1,000 ml |

As shown in FIG. 3, in the control system (a system with no glycerol and sugars), mean particle size was around 0.2 µm even after 30 repetitions of passing through the emulsifier. Also, mean particle sizes in the sorbitol-, xylitol- and fructose-containing systems were 0.18 to 0.2 μm even after 30 repetitions of passing through the emulsifier. On the contrary, in the case of the glycerol- and glucose-containing systems, the mean particle sizes decreased rapidly with the repetition of the emulsifier-passing. Thus, the mean particle size reached 0.17 μm after about 8 repetitions in the glycerol-containing system and after about 20 repetitions in the glucose-containing system. The results revealed that glycerol and glucose possess a high capacity to reduce particle size of emulsion.

EXAMPLE 4

A crude emulsion was prepared by adding 60 g of soybean oil, 7.2 g of egg yolk phospholipid and 500 g of glucose to water. The total volume was adjusted to 1,000 ml with water. The thus-obtained crude emulsion was subjected to emulsification using a Manton-Gaulin homogenizer (15M-8TA, manufactured by Gaulin) until its mean particle size reached 0.15 μm or below to prepare a fat emulsion. A 500 ml portion of the thus-obtained fat emulsion was mixed with 500 ml of water. The composition of the thus-prepared fat emulsion is shown in Table 5. A 50 ml capacity glass container was charged with this preparation and the air in the container was replaced by nitrogen gas followed by sealing. Thereafter, the thus-sealed container filled with the fat emulsion preparation was subjected to sterilization by autoclaving at 115° C. for 30 minutes. The appearance, pH values and mean particle sizes of the preparation before and after sterilization were compared, with the results shown in Table 6.

TABLE 5

| Component | Amount (g) |
|---|---|
| Soybean oil | 30 |
| Egg yolk phospholipid | 3.6 |
| Glucose | 250 |
| Distilled water for injection | necessary amount to adjust total volume to 1,000 ml |

TABLE 6

| Test item | Before sterilization | After sterilization |
|---|---|---|
| Appearance | white homogeneous emulsion | white homogeneous emulsion |
| pH | 5.60 | 5.01 |
| Mean particle size | 0.14 μm | 0.14 μm |

As shown in Table 6, emulsion conditions of the preparation were stable after sterilization, though its pH value decreased slightly.

EXAMPLE 5

After adding 429 ml of 70% glucose solution (70° C.) to a mixture consisting of 42.64 g soybean oil and 6.14 g egg yolk phospholipid (70° C.), the total volume of the resulting mixture was adjusted to 500 ml with water to prepare a crude emulsion. The thus-obtained crude emulsion was subjected to emulsification using a Manton-Gaulin homogenizer (15M-8TA, manufactured by Gaulin) under a pressure of 550 kg/cm$^2$ and at a temperature of 70° C. or below to obtain a fat emulsion having a mean particle size of 0.17 μm or below.

EXAMPLE 6

A 150 ml portion of the fat emulsion obtained in Example 5 was mixed with distilled water for injection to adjust the total volume to 500 ml. A 50 ml capacity glass container was charged with this preparation, and the air in the container was replaced by nitrogen gas followed by sealing. Thereafter, the thus-sealed container filled with the preparation was subjected to sterilization by autoclaving at 115° C. for 30 minutes. The thus-obtained preparation showed good emulsion conditions for a prolonged period of time.

EXAMPLE 7

A 200 ml portion of the fat emulsion obtained in Example 5 was mixed with 304 ml of distilled water for injection and 13.2 ml of 70% glucose solution. A 50 ml capacity glass container was charged with this preparation and the air in the container was replaced by nitrogen gas followed by sealing. Thereafter, the thus-sealed container filled with the preparation was subjected to sterilization at 115° C. for 30 minutes using an autoclave. The thus-obtained preparation showed good emulsion conditions for a prolonged period of time.

EXAMPLE 8

A mixture consisting of 60 g of soybean oil, 7.2 g of egg yolk phospholipid and an appropriate amount of water was stirred using a mixer, and the total volume was adjusted to 1,000 ml with water to obtain a crude emulsion. The resulting crude emulsion was subsequently emulsified using a Manton-Gaulin homogenizer (15M-8TA, manufactured by Gaulin). A 500 ml portion of the thus-obtained emulsion was mixed with 250 g of glucose and a predetermined amount of each buffer shown in Table 7, and the total volume was adjusted to 1,000 ml with distilled water for injection. Thereafter, the pH of the resulting emulsion was adjusted to 6 to obtain an infusion preparation. A 50 ml capacity glass container was charged with the infusion preparation and the air in the container was replaced by nitrogen gas followed by sealing. Thereafter, the thus-sealed container filled with the infusion preparation was subjected to sterilization by autoclaving at 115° C. for 30 minutes. The thus-sterilized infusion preparation was subjected to an accelerated preservation test at 80° C. for 48 hours to measure periodical changes in the pH value, mean particle size and free fatty acid concentration. The results are shown in Table 7.

TABLE 7

| | | | | Stored time (hr) at 80° C. | | | |
|---|---|---|---|---|---|---|---|
| Sample | Buffer | Conc. | Test item | 0 | 12 | 24 | 48 |
| Inven-tion | L-his-tidine/HCl | 0.01% | pH | 5.85 | 5.65 | 5.49 | 5.23 |
| | | | size (μm)** | 0.22 | 0.21 | 0.22 | 0.22 |
| | | | free fatty acid (mEq/l) | 0.71 | 0.83 | 1.08 | 2.11 |
| | | 0.02% | pH | 5.89 | 5.81 | 5.73 | 5.58 |
| | | | size (μm)** | 0.22 | 0.21 | 0.21 | 0.22 |
| | | | free fatty acid (mEq/l) | 0.83 | 0.83 | 1.20 | 1.71 |
| | | 0.05% | pH | 5.89 | 5.78 | 5.68 | 5.50 |
| | | | size (μm)** | 0.21 | 0.21 | 0.21 | 0.22 |
| | | | free fatty acid (mEq/l) | 0.83 | 0.83 | 1.32 | 1.88 |
| | Tris/HCl | 1 mM | pH | 5.68 | 4.99 | 4.75 | 4.55 |
| | | | size (μm)** | 0.21 | 0.21 | 0.21 | 0.22 |
| | | | free fatty acid (mEq/l) | 0.71 | 0.83 | 1.69 | 2.50 |
| Control | None | | pH | 5.29 | 4.68 | 4.58 | 4.38 |
| | | | size (μm)** | 0.20 | 0.22 | 0.21 | 0.22 |
| | | | free fatty acid (mEq/l) | 0.59 | 0.83 | 1.81 | 3.45 |
| Com- | KH$_2$PO$_4$/ | 1 mM | pH | 5.10 | 4.77 | 4.61 | 4.39 |

TABLE 7-continued

| Sample | Buffer | Conc. | Test item | \multicolumn{4}{c}{Stored time (hr) at 80° C.} |
| --- | --- | --- | --- | --- | --- | --- | --- |
| | | | | 0 | 12 | 24 | 48 |
| parison | $K_2HPO_4$ | | size (μm)** | 0.22 | 0.22 | 0.21 | 0.21 |
| | | | free fatty acid (mEq/l) | 0.71 | 0.83 | 1.93 | 3.45 |
| | $K_2HPO_4$/ citric | 1 mM | pH | 5.05 | 4.75 | 4.60 | 4.41 |
| | | | size (μm)** | 0.21 | 0.22 | 0.21 | 0.22 |
| | | | free fatty acid (mEq/l) | 1.08 | 0.71 | 1.93 | 3.75 |

**mean particle size (μm)

As is evident from the results shown in Table 7, the preparation of the present invention has excellent effect to prevent a decrease in pH values and an increase in free fatty acids, while a more pronounced decrease in pH values and a sharp increase in free fatty acids are observed in the control and comparative examples. Thus, it was confirmed that the infusion preparation of the present invention has markedly excellent stability.

EXAMPLE 9

A mixture consisting of 60 g of soybean oil, 7.2 g of egg yolk phospholipid and an appropriate amount of water was stirred using a mixer, and the total volume was adjusted to 1,000 ml with water to obtain a crude emulsion. The resulting crude emulsion was subsequently emulsified using a Manton-Gaulin homogenizer (15M-8TA, manufactured by Gaulin). A 500 ml portion of the thus-obtained emulsion was mixed with 250 g of glucose, 0.2 g of L-histidine and 1 g of thioglycerol, and the total volume was adjusted to 1,000 ml with distilled water for injection. Thereafter, the pH of the resulting emulsion was adjusted to 6 to obtain an infusion preparation. The composition of the resulting infusion preparation is shown in Table 8.

A 50 ml capacity glass container was charged with the infusion preparation and the air in the container was replaced by nitrogen gas followed by sealing. Thereafter, the thus-sealed container filled with the infusion preparation was subjected to sterilization by autoclaving at 115° C. for 30 minutes. Thereafter, the appearance, pH values, mean particle sizes and free fatty acid concentrations before and after sterilization were measured with the results shown in Table 9.

TABLE 8

| Component | Amount (g) |
| --- | --- |
| Soybean oil | 30 |
| Egg yolk phospholipid | 3.6 |
| Glucose | 250 |
| L-Histidine | 0.2 |
| Thioglycerol | 1 |
| Distilled water for injection | necessary amount to adjust total volume to 1,000 ml |

TABLE 9

| Test item | Before sterilization | After sterilization |
| --- | --- | --- |
| Appearance | white homogeneous emulsion | white homogeneous emulsion |
| pH | 5.60 | 5.21 |
| Mean particle size | 0.22 μm | 0.22 μm |
| Free fatty acid conc. | 0.59 mEq/l | 0.71 mEq/l |

As shown in Table 9, pH value decreased slightly and free fatty acid concentration increased a little by sterilization, but the preparation maintained its emulsified conditions stably.

EXAMPLE 10

A mixture consisting of 60 g of soybean oil, 7.2 g of egg yolk phospholipid, 500 g of glucose and an appropriate amount of water was stirred using a mixer, and the total volume was adjusted to 1,000 ml with water to obtain a crude emulsion. The resulting crude emulsion was subsequently emulsified using a Manton-Gaulin homogenizer (15M-8TA, manufactured by Gaulin). A 500 ml portion of the thus-obtained emulsion was mixed with 0.2 g of L-histidine and 1 g of thioglycerol, and the total volume was adjusted to 1,000 ml with water. Thereafter, the pH of the resulting emulsion was adjusted to 6 to obtain an infusion preparation. A 50 ml capacity glass container was charged with the infusion preparation, and the air in the container was replaced by nitrogen gas followed by sealing. Thereafter, the thus-sealed container filled with the infusion preparation was subjected to sterilization by autoclaving at 115° C. for 30 minutes. Thereafter, the appearance, pH values, mean particle sizes and free fatty acid concentrations before and after sterilization were measured with the results shown in Table 10.

TABLE 10

| Test item | Before sterilization | After sterilization |
| --- | --- | --- |
| Appearance | white homogeneous emulsion | white homogeneous emulsion |
| pH | 5.71 | 5.32 |
| Mean particle size | 0.14 μm | 0.14 μm |
| Free fatty acid conc. | 0.50 mEq/l | 0.65 mEq/l |

As shown in Table 10, pH value decreased slightly and free fatty acid concentration increased a little after sterilization, but the preparation maintained its emulsified conditions stably.

EXAMPLE 11

(A) Infusion Preparations and Stability Tests

Four infusion preparations enclosed in glass containers (3 samples for each) having the respective compositions shown in Table 11 were prepared in a manner similar to the procedure of Example 10. Using these preparations, stability tests were carried out under the following conditions.

Storage temperature: 40° C.

Humidity: 75%

Stored period: 0, 1, 2 and 3 months

TABLE 11

| Component | Amount (g) |
|---|---|
| Soybean oil | 33 |
| Egg yolk phospholipid | 4.8 |
| Glucose | 250 |
| L-Histidine | 0, 0.05, 0.1 or 0.15 |
| Distilled water for injection | necessary amount to adjust total volume to 1,000 ml |

(B) Test Results

As shown below, the stability of the infusion preparation in which a fat emulsion was blended with a reducing sugar was improved considerably by the addition of L-histidine.

(i) Appearance

All the tested preparations showed a white and homogeneously emulsified appearance throughout the storing period.

(ii) pH

Table 12 shows pH values of each preparation at the time of the commencement of the testing and during storage. In the table, each pH value is expressed as an average of three samples.

As shown in Table 12, a decrease in the pH value was repressed in proportion to the concentration of L-histidine.

TABLE 12

| Concentration of | pH | | | |
|---|---|---|---|---|
| | Zero | Stored months at 40° C. | | |
| L-histidine (%) | time | 1 | 2 | 3 |
| 0 | 4.33 | 4.58 | 4.58 | 4.46 |
| 0.005 | 5.19 | 5.37 | 5.24 | 5.11 |
| 0.01 | 5.64 | 5.65 | 5.54 | 5.43 |
| 0.015 | 5.80 | 5.84 | 5.70 | 5.58 |

(iii) Mean Particle Size

Table 13 shows the mean particle sizes of each preparation at the time of commencement of the testing and during storage. In the table, each mean particle size (unit, μm) is expressed as an average of three samples.

As shown in Table 13, the mean particle size in each preparation hardly changed throughout the stored period.

TABLE 13

| Concentration of | Mean particle size (μm) | | | |
|---|---|---|---|---|
| | Zero | Stored months at 40° C. | | |
| L-histidine (%) | time | 1 | 2 | 3 |
| 0 | 0.15 | 0.15 | 0.16 | 0.16 |
| 0.005 | 0.15 | 0.15 | 0.16 | 0.17 |
| 0.01 | 0.16 | 0.16 | 0.16 | 0.17 |
| 0.015 | 0.16 | 0.15 | 0.16 | 0.17 |

(iv) Free Fatty Acid Concentration

Table 14 shows free fatty acid concentrations of each preparation at the time of commencement of the testing and during storage. In the table, each free acid concentration (unit, mEq/l) is expressed as an average of three samples.

As shown in Table 14, an increase in the free fatty acid concentration was repressed in proportion to the concentration of L-histidine.

TABLE 14

| Concentration of | Concentration of free fatty acid (mEq/l) | | | |
|---|---|---|---|---|
| | Zero | Stored months at 40° C. | | |
| L-histidine (%) | time | 1 | 2 | 3 |
| 0 | 1.62 | 2.26 | 3.47 | 3.80 |
| 0.005 | 0.62 | 0.91 | 1.69 | 2.16 |
| 0.01 | 0.40 | 0.77 | 1.20 | 1.64 |
| 0.015 | 0.40 | 0.70 | 0.99 | 1.43 |

EXAMPLE 12

A mixture consisting of 79.2 g of soybean oil, 9.5 g of egg yolk phospholipid and 600 g of glucose was adjusted to a total volume of 1,000 ml with water, and the resulting mixture was emulsified using a Manton-Gaulin homogenizer (15M-8TA, manufactured by Gaulin). The thus-obtained emulsion was diluted with 2.4 volumes of water and filtered. A 50 ml capacity glass bottle was charged with the thus-diluted emulsion, and the air in the bottle was replaced by nitrogen gas followed by sealing. Thereafter, the thus-sealed bottle filled with the diluted emulsion was subjected to sterilization by autoclaving at 115° C. for 30 minutes. The preparation thus obtained is called "sugar-added fat emulsion" hereinafter.

Separately from this, a solution containing amino acids and electrolytes as shown in Table 15 was prepared and divided into separate portions. After adding 0 to 80 mEq/l of citric acid to separate portions of the solution, each of the resulting solutions was filtered. A 50 ml capacity glass bottle was charged with the resulting filtrate, and the air in the bottle was replaced by nitrogen gas followed by sealing. Thereafter, the thus-sealed bottle filled with the diluted emulsion was subjected to sterilization by autoclaving at 115° C. for 30 minutes. The preparation thus obtained is called "amino acid+electrolyte solution" hereinafter. Each of the thus prepared solutions was adjusted to pH 6.3 to 6.4.

A 2 ml portion of the amino acid+electrolyte solution was taken out aseptically from the bottle and transferred into a 15 ml capacity sterile polystyrene tube. Next, 4 ml of the sugar-added fat emulsion was taken out aseptically from its bottle and transferred into the polystyrene tube and the solution and the emulsion were mixed followed by sealing the tube. Changes in the turbidity, mean particle size and appearance of the thus prepared mixture were measured over one week, with respect to the concentration of citric acid in the amino acid+electrolyte solution, with the results shown in Table 16. In this instance, the mean particle size of the fat emulsion was measured by a light scattering method, and turbidity was expressed as absorbance at 620 nm (1 cm cell).

TABLE 15

| Component | Concentration (per liter) |
|---|---|
| Electrolytes | |
| sodium chloride | 1.949 g |
| potassium chloride | 3.500 g |
| magnesium sulfate.7H$_2$O | 2.054 g |
| calcium gluconate.H$_2$O | 6.352 g |
| dipotassium glycerophosphate (50%) | 10.688 g |
| sodium acetate.3H$_2$O | 11.340 g |
| zinc sulfate.7H$_2$O | 9.585 mg |

TABLE 15-continued

| Component | Concentration (per liter) |
|---|---|
| Amino acids | |
| L-isoleucine | 8.000 g |
| L-leucine | 14.000 g |
| L-valine | 8.000 g |
| L-lysine.HCl | 10.000 g |
| L-methionine | 4.000 g |
| L-phenylalanine | 8.000 g |
| L-threonine | 6.000 g |
| L-tryptophan | 1.200 g |
| L-arginine | 10.500 g |
| L-histidine | 5.000 g |
| glycine | 5.300 g |
| L-alanine | 8.500 g |
| L-proline | 6.000 g |
| L-aspartic acid | 1.500 g |
| L-serine | 3.000 g |
| L-tyrosine | 0.500 g |
| L-glutamic acid | 1.500 g |
| N-acetyl-L-cysteine | 1.100 g |
| Other ingredient | |
| distilled water for injection | proper amount |

TABLE 16

| Test item | Citric acid conc. | 0 hr. | 24 hr. | 48 hr. | 1 week |
|---|---|---|---|---|---|
| Turbidity | 0 mEq/l | 0.034 | 0.083 | 0.098 | 0.097 |
| | 13 mEq/l | 0.033 | 0.055 | 0.063 | 0.080 |
| | 20 mEq/l | 0.033 | 0.050 | 0.057 | 0.069 |
| | 27 mEq/l | 0.034 | 0.063 | 0.070 | 0.085 |
| Mean particle size ($\mu$m) | 0 mEq/l | 0.152 | 0.187 | 0.194 | 0.200 |
| | 13 mEq/l | 0.152 | 0.170 | 0.173 | 0.177 |
| | 20 mEq/l | 0.148 | 0.165 | 0.174 | 0.179 |
| | 27 mEq/l | 0.155 | 0.173 | 0.180 | 0.189 |
| Appearance* | 0 mEq/l | N | C | C | D |
| | 13 mEq/l | N | A | B | D |
| | 20 mEq/l | N | N | A | B |
| | 27 mEq/l | N | N | A | C |

*:
A, slight coagulation;
B, obvious coagulation;
C, coagulation and oil drops;
D, considerable coagulation and oil drops; and
N, no change As shown in Table 16, an increase in the turbidity and mean particle size was repressed by the addition of citric acid, with only slight changes in appearance.

EXAMPLE 13

In a stream of nitrogen, each of the predetermined amounts of amino acids and electrolytes shown in Tables 17 and 18 was dissolved in distilled water for injection maintained at 80° C., and the resulting solution was adjusted to pH 6.2 with citric acid. After filtering the solution, resulting filtrate was put into a nitrogen-replaced glass bottle and sterilized by autoclaving at 115° C. for 30 minutes. Using the thus-sterilized preparation, an accelerated preservation test was carried out. Thus, the appearance, coloring degrees and pH values of the filtrate were measured immediately after sterilization and after the preservation at 80° C. for 48 hours. The results are shown in Table 19. In this instance, coloring degree was expressed as absorbance at 450 nm (5 cm cell).

TABLE 17

| Component | Concentration (per liter) |
|---|---|
| L-isoleucine | 8.000 g |
| L-leucine | 14.000 g |
| L-valine | 8.000 g |
| L-lysine.HCl | 10.000 g |
| L-methionine | 4.000 g |
| L-phenylalanine | 8.000 g |
| L-threonine | 6.000 g |
| L-tryptophan | 1.200 g |
| L-arginine | 10.500 g |
| L-histidine | 5.000 g |
| glycine | 5.300 g |
| L-alanine | 8.500 g |
| L-proline | 6.000 g |
| L-aspartic acid | 1.500 g |
| L-serine | 3.000 g |
| L-tyrosine | 0.500 g |
| L-glutamic acid | 1.500 g |
| N-acetyl-L-cysteine | 1.100 g |

TABLE 18

| Component | Concentration (per liter) |
|---|---|
| Sodium chloride | 1.949 g |
| Potassium chloride | 3.500 g |
| Magnesium sulfate.7H$_2$O | 2.054 g |
| Calcium gluconate.H$_2$O | 6.352 g |
| Dipotassium glycerophosphate (50%) | 10.688 g |
| Sodium acetate.3H$_2$O | 11.340 g |
| Zinc sulfate. 7H$_2$O | 9.585 mg |

TABLE 19

| Test item | Just after sterilization | 48 hours after storage at 80° C. |
|---|---|---|
| Appearance | colorless & clear | colorless & clear |
| Color degree | 0.001 | 0.005 |
| pH | 6.23 | 6.25 |

As shown in Table 19, the sterilized infusion preparation of the present invention was colorless and clear, with no precipitation and well repressed coloring and pH changes. Even after preservation at 80° C. for 48 hours, the preparation was colorless and clear and coloring and pH changes were repressed. Thus, it is evident that the infusion preparation of the present invention has markedly high stability.

EXAMPLE 14

An infusion preparation was obtained in the same manner as in the procedure of Example 13 except that the electrolyte composition of Table 18 was replaced by another composition shown in Table 20. Using the thus-obtained preparation, an accelerated preservation test was carried out. Thus, the appearance, coloring degrees and pH values of the filtrate were measured immediately after sterilization and after the preservation at 80° C. for 48 hours. As in the case of the infusion preparation of Example 13, the preparation of this instance showed markedly high stability.

TABLE 20

| Component | Concentration (per liter) |
| --- | --- |
| Sodium chloride | 1.949 g |
| Potassium chloride | 4.302 g |
| Magnesium sulfate.7H$_2$O | 2.054 g |
| Calcium gluconate.H$_2$O | 6.352 g |
| Dipotassium glycerophosphate (50%) | 8.016 g |
| Sodium acetate.3H$_2$O | 11.340 g |
| Zinc sulfate.7H$_2$O | 9.585 mg |

EXAMPLE 15

A mixture consisting of 79.2 g of soybean oil, 11.4 g of egg yolk phospholipid and 600 g of glucose was adjusted to a total volume of 1,000 ml with distilled water for injection, and the resulting mixture was emulsified using a Manton-Gaulin homogenizer (15M-8TA, manufactured by Gaulin). The thus-obtained emulsion was diluted with 2.4 volumes of water. A 50 ml capacity glass bottle was charged with the thus-diluted emulsion and the air in the bottle was replaced by nitrogen gas followed by sealing. Thereafter, the thus-sealed bottle filled with the diluted emulsion was subjected to sterilization by autoclaving at 115° C. for 30 minutes. The preparation thus obtained is called "sugar-added fat emulsion" hereinafter. This fat emulsion showed a mean fat particle size of 0.16 μm.

A 2 ml portion of the infusion preparation containing amino acids and electrolytes obtained in Example 13 was taken out aseptically and transferred into a 15 ml capacity sterile polystyrene tube. Next, 4 ml of the above-described sugar-added fat emulsion was taken out aseptically and transferred into the polystyrene tube, and the preparation and the emulsion were mixed followed by sealing the tube. Changes in the turbidity, mean particle size and appearance of the thus-prepared mixture were measured over 48 hours, with the results shown in Table 21. In this instance, turbidity was expressed as absorbance at 620 nm (1 cm cell) and mean particle size of the fat emulsion was measured by a light scattering method.

TABLE 21

| Test item | After mixing | After 24 hr. | After 48 hr. |
| --- | --- | --- | --- |
| Turbidity | 0.034 | 0.034 | 0.036 |
| Mean particle size | 0.15 μm | 0.16 μm | 0.16 μm |
| Appearance | homogeneous | homogeneous | homogeneous |

As is evident from the results shown in Table 21, the infusion preparation of the present invention does not spoil the stability of a fat emulsion after it is mixed with the solution containing amino acids and electrolytes.

EXAMPLE 16

(1) Preparation of Infusion Liquid Containing Fat Emulsion and Sugar

A 66 g portion of soybean oil, 9.5 g of egg yolk phospholipid and 500 g of glucose were added to an appropriate volume of water, and the mixture was stirred using a mixer and then adjusted to a total volume of 1,000 ml with distilled water for injection to obtain a crude emulsion. The thus-obtained crude emulsion was emulsified using a Manton-Gaulin homogenizer (15M-8TA, manufactured by Gaulin) to obtain an emulsion having a mean particle size of 0.17 μm or less. Water was added to a 500 ml portion of the resulting emulsion to make the total volume 1,000 ml. The composition of the thus-obtained infusion liquid is shown in Table 22.

TABLE 22

| Component | Amount (g) |
| --- | --- |
| Soybean oil | 33 |
| Egg yolk phospholipid | 4.75 |
| Glucose | 250 |
| Distilled water for injection | necessary amount to adjust total volume to 1,000 ml |

(2) Preparation of Infusion Liquid Containing Amino Acids and Electrolytes

In a stream of nitrogen, the respective amounts of amino acids and electrolytes shown in Tables 23 and 24 were dissolved in distilled water for injection maintained at 80° C. The resulting solution was adjusted to pH 6.2 with citric acid.

TABLE 23

| Component | Concentration (per liter) |
| --- | --- |
| L-isoleucine | 8.000 g |
| L-leucine | 14.000 g |
| L-valine | 8.000 g |
| L-lysine.HCl | 10.000 g |
| L-methionine | 4.000 g |
| L-phenylalanine | 8.000 g |
| L-threonine | 6.000 g |
| L-tryptophan | 1.200 g |
| L-arginine | 10.500 g |
| L-histidine | 5.000 g |
| glycine | 5.300 g |
| L-alanine | 8.500 g |
| L-proline | 6.000 g |
| L-aspartic acid | 1.500 g |
| L-serine | 3.000 g |
| L-tyrosine | 0.500 g |
| L-glutamic acid | 1.500 g |
| N-acetyl-L-cysteine | 1.100 g |

TABLE 24

| Component | Concentration (per liter) |
| --- | --- |
| Sodium chloride | 1.949 g |
| Potassium chloride | 4.302 g |
| Magnesium sulfate.7H$_2$O | 2.054 g |
| Calcium gluconate.H$_2$O | 6.352 g |
| Dipotassium glycerophosphate (50%) | 8.016 g |
| Sodium acetate.3H$_2$O | 11.340 g |
| Zinc sulfate.7H$_2$O | 9.585 mg |

(3) Sterilization and Preparation of the Infusion of the Invention

A polypropylene container having a structure as shown in FIG. 1 was used. After closing the communicating means 6 with the pinch cock 7, 600 ml of the infusion liquid containing a fat emulsion and a sugar obtained in the above procedure (1) was injected into the first compartment 2 from the port 8 with nitrogen gas charging, subsequently sealing the port 8. In the same manner, 300 ml of the infusion liquid containing amino acids and electrolytes obtained in the above procedure (2) was injected into the second compartment 3 from the port 9 with nitrogen gas charging, subsequently sealing the port 9. The thus-prepared container 1 was sterilized by autoclaving at 115° C. for 30 minutes, followed by cooling to room temperature.

After sterilization, the pinch cock 7 was removed from the communicating means 6, and the infusion liquids in the first and second compartments 2 and 3 were mixed thoroughly through the communicating means 6 to obtain an infusion preparation of the present invention. The composition of the thus-obtained infusion preparation is shown in Table 25.

TABLE 25

| Composition | Infusion preparations of: | |
|---|---|---|
| | Example 16 (per liter) | Example 17 (per liter) |
| Fat | | |
| soybean oil | 17.33 g | 22.00 g |
| egg yolk phospholipid | 2.49 g | 3.17 g |
| Sugar | | |
| glucose | 122.00 g | 166.67 g |
| Amino acids | | |
| L-isoleucine | 2.67 g | 2.67 g |
| L-leucine | 4.67 g | 4.67 g |
| L-valine | 2.67 g | 2.67 g |
| L-lysine.HCl | 3.33 g | 3.33 g |
| L-methionine | 1.33 g | 1.33 g |
| L-phenylalanine | 2.67 g | 2.67 g |
| L-threonine | 2.00 g | 2.00 g |
| L-tryptophan | 0.40 g | 0.40 g |
| L-arginine | 3.50 g | 3.50 g |
| L-histidine | 1.67 g | 1.67 g |
| glycine | 1.77 g | 1.77 g |
| L-alanine | 2.83 g | 2.83 g |
| L-proline | 2.00 g | 2.00 g |
| L-aspartic acid | 0.50 g | 0.50 g |
| L-serine | 1.00 g | 1.00 g |
| L-tyrosine | 0.17 g | 0.17 g |
| L-glutamic acid | 0.50 g | 0.50 g |
| N-acetyl-L-cysteine | 0.37 g | 0.37 g |
| Electrolytes | | |
| Sodium | 38.89 mEq | 38.89 mEq |
| Potassium | 30.00 mEq | 30.00 mEq |
| Calcium | 9.44 mEq | 9.44 mEq |
| Magnesium | 5.56 mE | 5.56 mEq |
| Chlorine | 48.60 mEq | 45.17 mEq |
| Phosphorus | 5.37 mEq | 7.17 mEq |
| Zinc | 11.11 μmol | 11.11 μmol |
| Other ingredient | | |
| Citric acid | 1.401 g | 1.401 g |

(4) Stability Tests of the Infusion Preparation

The infusion preparation of the present invention obtained in the above procedure (3) was stored at 25° C. for one week, and changes in appearance, mean fat particle size and turbidity during the storage were measured. The results are shown in Table 26. In this instance, a control infusion preparation was obtained by repeating the above procedures except that 300 ml of distilled water for injection was enclosed in the second compartment 3. Mean particle size of the fat emulsion was measured by a light scattering method, and turbidity was expressed as absorbance at 620 nm (1 cm cell).

TABLE 26

| | Stored time | | | |
|---|---|---|---|---|
| Test item | After mixing | After 24 hr | After 48 hr | After 1 week |
| Invention | | | | |

TABLE 26-continued

| | Stored time | | | |
|---|---|---|---|---|
| Test item | After mixing | After 24 hr | After 48 hr | After 1 week |
| Appearance | homogeneous | homogeneous | homogeneous | homogeneous |
| Mean particle size | 0.15 μm | 0.16 μm | 0.16 μm | 0.16 μm |
| Turbidity | 0.034 | 0.034 | 0.030 | 0.040 |
| Control | | | | |
| Appearance | homogeneous | homogeneous | homogeneous | homogeneous |
| Mean particle size | 0.16 μm | 0.16 μm | 0.16 μm | 0.16 μm |
| Turbidity | 0.034 | 0.031 | 0.031 | 0.036 |

As shown in Table 26, no changes in appearance, particle size or turbidity were found in the preparation of the invention during the preservation period, thus confirming high stability of the preparation of the invention.

EXAMPLE 17

An infusion liquid having the composition shown in the following Table 27 was prepared in accordance with the procedure (1) of Example 16.

TABLE 27

| Component | Amount (g) |
|---|---|
| Soybean oil | 26 |
| Egg yolk phospholipid | 3.74 |
| Glucose | 183 |
| Distilled water for injection | necessary amount to adjust total volume to 1,000 ml |

An infusion preparation was obtained by repeating the process of Example 16 except that the sugar-containing fat emulsion of Table 27 was used instead of the fat emulsion of Table 22, and an electrolyte solution shown in the following Table 28 was used instead of the electrolyte solution of Table 24. The composition of the thus-obtained infusion preparation is shown in Table 25.

TABLE 28

| Component | Concentration (per liter) |
|---|---|
| Sodium chloride | 1.949 g |
| Potassium chloride | 3.500 g |
| Magnesium sulfate.7H$_2$O | 2.054 g |
| Calcium gluconate.H$_2$O | 6.352 g |
| Dipotassium glycerophosphate (50%) | 10.688 g |
| Sodium acetate.3H$_2$O | 11.340 g |
| Zinc sulfate.7H$_2$O | 9.585 mg |

Stability tests of the thus-prepared infusion preparation were carried out in the same manner as in Example 16. Excellent stability was found in the preparation, as in the case of the infusion preparation of Example 16.

EXAMPLE 18

An appropriate volume of distilled water for injection was added to a mixture of 66 g of soybean oil with 9.5 g of egg yolk phospholipid, and the resulting mixture was stirred using a mixer and then adjusted to a total volume of 1,000 ml with distilled water for injection to obtain a crude emulsion. The thus-obtained crude emulsion was emulsified using a Manton-Gaulin homogenizer (15M-8TA, manufactured by Gaulin) to obtain a fat emulsion. A 500 ml portion of the resulting emulsion was mixed with 250 g of glucose, and the total volume of the mixture was adjusted to 1,000 ml with distilled water for injection. The composition of the thus obtained fat emulsion is shown in Table 29.

TABLE 29

| Component | Amount (g) |
| --- | --- |
| Soybean oil | 33 |
| Egg yolk phospholipid | 4.75 |
| Glucose | 250 |
| Distilled water for injection | necessary amount to adjust total volume to 1,000 ml |

An infusion preparation was obtained by repeating the process of Example 16 except that the fat emulsion of Table 29 was used instead of the fat emulsion of Table 22.

Stability tests of the thus-prepared infusion preparation were carried out in the same manner as in Example 16. Excellent stability was found in the preparation, as in the case of the infusion preparation of Example 16.

While the invention has been described in detail and with reference to specific examples thereof, it will be apparent to one skilled in the art that various changes and modifications can be made therein without departing from the spirit and scope thereof.

What is claimed is:

1. An infusion preparation consisting essentially of an infusion liquid containing a fat emulsion, an anti-coloring agent selected from the group consisting of thioglycerol and dithiothreitol, and a reducing sugar, wherein said fat is contained in an amount of from 0.1 to 30% (w/v), said emulsifying agent used as an emulsifying agent for said fat emulsion is contained in an amount of from 0.01 to 10% (w/v) and said reducing sugar is contained in an amount of from 5 to 60% (w/v).

2. The infusion preparation according to claim 1, wherein said fat is a member selected from the group consisting of plant oils, fish oils, medium-chain fatty acid triglycerides and chemically synthesized triglycerides, and mixtures thereof, said emulsifying agent is a member selected from the group consisting of egg yolk phospholipids, hydrogenated egg yolk phospholipids, soybean phospholipids, hydrogenated soybean phospholipids and nonionic surface active agents, and mixtures thereof, and said reducing sugar as a sugar source is a reducing sugar selected from the group consisting of glucose, fructose and maltose, and mixtures thereof, or a mixture of said reducing sugar with at least one compound selected from the group consisting of sorbitol, xylitol and glycerol.

3. The infusion preparation according to claim 1, wherein said anti-coloring agent is contained in an amount of 1% or less (w/v).

4. The infusion preparation according to claim 1, which further comprises a buffer selected from the group consisting of L-histidine and tris(hydroxymethyl)aminomethane.

5. The infusion preparation according to claim 4, wherein said buffer is contained in an amount of from 0.001 to 1.0% (w/v).

6. An infusion preparation comprising an infusion liquid containing a fat emulsion having a mean particle size of 0.17 µm or less and a sugar, which infusion liquid comprises a buffer agent selected from the group consisting of L-histidine and tris(hydroxymethyl)aminomethane, and mixtures thereof.

7. An infusion preparation comprising an infusion liquid containing a fat emulsion and a reducing sugar, wherein said fat is contained in an amount of from 0.1 to 30% (w/v), said emulsifying agent used as an emulsifying agent for said fat emulsion is contained in an amount of from 0.01 to 10% (w/v), said reducing sugar is contained in an amount of from 5 to 60% (w/v), and said fat emulsion has a mean particle size of 0.17 µm or less.

8. The infusion preparation according to claim 7, wherein said fat is a member selected from the group consisting of plant oils, fish oils, medium-chain fatty acid triglycerides and chemically synthesized triglycerides, and mixtures thereof, said emulsifying agent is a member selected from the group consisting of egg yolk phospholipids, hydrogenated egg yolk phospholipids, soybean phospholipids, hydrogenated soybean phospholipids and nonionic surface active agents, and mixtures thereof, and said reducing sugar as a sugar source is a reducing sugar selected from the group consisting of glucose, fructose and maltose, and mixtures thereof, or a mixture of said reducing sugar with at least one compound selected from the group consisting of sorbitol, xylitol and glycerol.

9. The infusion preparation according to claim 7, which further comprises an anti-coloring agent selected from the group consisting of thioglycerol and dithiothreitol.

10. The infusion preparation according to claim 9, wherein said anti-coloring agent is contained in an amount of 1% or less (w/v).

11. The infusion preparation according to claim 7, which further comprises a buffer selected from the group consisting of L-histidine and tris(hydroxymethyl)aminomethane.

12. The infusion preparation according to claim 11, wherein said buffer is contained in an amount of from 0.001 to 1.0% (w/v).

13. An infusion preparation consisting essentially of an infusion liquid containing a fat emulsion and a reducing sugar, wherein said fat is contained in an amount of from 0.1 to 30% (w/v), said emulsifying agent used as an emulsifying agent for said fat emulsion is contained in an amount of from 0.01 to 10% (w/v) and said reducing sugar is contained in an amount of from 5 to 60% (w/v), and wherein said fat emulsion has a mean particle size of 0.17 µm or less.

\* \* \* \* \*